(12) United States Patent
Ward et al.

(10) Patent No.: US 12,421,994 B2
(45) Date of Patent: Sep. 23, 2025

(54) JUNCTIONAL HEMORRHAGE OCCLUSION DEVICE

(71) Applicant: THE REGENTS OF THE UNIVERSITY OF MICHIGAN, Ann Arbor, MI (US)

(72) Inventors: Kevin Ward, Glen Allen, VA (US); Jeffrey Stephen Plott, Algonac, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 481 days.

(21) Appl. No.: 17/911,240

(22) PCT Filed: Mar. 17, 2021

(86) PCT No.: PCT/US2021/022731
§ 371 (c)(1),
(2) Date: Sep. 13, 2022

(87) PCT Pub. No.: WO2021/188649
PCT Pub. Date: Sep. 23, 2021

(65) Prior Publication Data
US 2023/0098316 A1 Mar. 30, 2023

Related U.S. Application Data

(60) Provisional application No. 62/990,756, filed on Mar. 17, 2020.

(51) Int. Cl.
*A61B 17/132* (2006.01)
*E21B 17/043* (2006.01)
(Continued)

(52) U.S. Cl.
CPC .......... *F16B 39/22* (2013.01); *A61B 17/1325* (2013.01); *E21B 17/043* (2013.01);
(Continued)

(58) Field of Classification Search
CPC .............. A61B 17/132; A61B 17/1322; A61B 17/1325; A61B 17/1327; A61B 17/135;
(Continued)

(56) References Cited

U.S. PATENT DOCUMENTS 1,936,855 A * 11/1933 Powers ...................... A61F 5/32
128/116.1
2,557,309 A * 6/1951 Pease ........................ A61F 5/30
128/113.1
(Continued)

FOREIGN PATENT DOCUMENTS

CN         105105816 A    12/2015
WO    WO-2016179976 A1    11/2016

OTHER PUBLICATIONS

Extended European Search Report from European Application No. 21771596.0 dated Feb. 23, 2024.
(Continued)

*Primary Examiner* — Kathleen S Holwerda
(74) *Attorney, Agent, or Firm* — MARSHALL, GERSTEIN & BORUN LLP

(57) ABSTRACT

A junctional hemorrhage control device includes a strap and a base operably connected to the strap. A strap carriage is operably connected to, and linearly translatable relative to, the base. A screw assembly is rotatably attached to the base. The screw assembly moves the strap carriage away from the base when the screw assembly is operated in one direction and towards the base when the screw assembly is operated
(Continued)

in an opposite direction. A removable pressure plate is attached to the base to apply occlusion pressure to a hemorrhage location.

18 Claims, 4 Drawing Sheets

(51) Int. Cl.
*F16B 39/22* (2006.01)
*A61B 17/12* (2006.01)
*A61F 13/00* (2006.01)
*A61F 13/14* (2006.01)

(52) U.S. Cl.
CPC ............... *A61B 2017/12004* (2013.01); *A61F 2013/0028* (2013.01); *A61F 13/148* (2013.01)

(58) Field of Classification Search
CPC .......... A61B 17/1355; A61F 5/30; A61F 5/32; A61F 5/34; A61H 39/04
See application file for complete search history.

(56) References Cited

U.S. PATENT DOCUMENTS

| | | | |
|---|---|---|---|
| 3,933,150 A | 1/1976 | Kaplan et al. | |
| 5,139,512 A | 8/1992 | Dreiling et al. | |
| 5,514,155 A * | 5/1996 | Daneshvar | A61B 17/1325 |
| | | | 602/53 |
| 7,329,792 B2 | 2/2008 | Buckman et al. | |
| 2005/0125025 A1 | 6/2005 | Rioux | |
| 2012/0150215 A1* | 6/2012 | Donald | A61B 17/1325 |
| | | | 606/203 |
| 2013/0296921 A1* | 11/2013 | Saunders | A61B 17/1325 |
| | | | 606/203 |
| 2015/0051638 A1 | 2/2015 | Dickinson et al. | |
| 2018/0193030 A1* | 7/2018 | Ward | A61B 17/1325 |

OTHER PUBLICATIONS

Search Report for International application No. PCT/US21/22731 mailed Jul. 8, 2021.
Written Opinion for International application No. PCT/US21/22731 mailed Jul. 8, 2021.

* cited by examiner

JUNCTIONAL HEMORRHAGE OCCLUSION DEVICE

FIELD OF THE INVENTION

The invention generally relates to hemorrhage occlusion devices and more specifically to portable compact junctional hemorrhage occlusion devices capable of controlling hemorrhage at anatomical junctional sites not amendable to treatment with traditional tourniquets.

BACKGROUND OF THE INVENTION

Hemorrhage from vascular injuries in the extremities, such as the arms and legs, and/or from vascular injuries in the pelvis or abdomen can be difficult to treat by a single person. While the treatment of such injuries is challenging when they occur in civilian populations, treatment may be even more difficult in combat situations. Improvements in body armor have reduced mortality from combat injuries to the chest. However, the incidence of injuries to the extremities, pelvis, abdomen, axillary, and groin areas, and the associated mortality rates, remain high. Recent efforts have developed better hemorrhage control devices for treatment of these wounds.

Wounds to the axilla, groin, pelvis, and abdomen are complex and may involve several systems either alone or in combination, including major vascular structures, the bony pelvis, solid organs such as the liver and spleen, and even hollow organ injury to the bowel and bladder. Wounds directly involving isolated major vascular structures above the level of the femoral artery and vein such as the iliac artery and veins are most challenging to deal with followed by complex bony pelvic injuries from high velocity penetrating trauma resulting in complex arterial and lower pressure venous bleeding similar to those of blunt pelvic injuries experienced in a civilian trauma center.

Controlling hemorrhage by application of direct manual pressure may be particularly challenging in cases where the injured person is alone. In fact, most current tourniquet devices are designed to be applied "one-handed." However, it can be difficult and very painful to achieve a tourniquet pressure that stops blood flow with current tourniquet devices.

Even injuries involving isolated major vascular injury at or just above the inguinal ligament pose a tremendous field challenge in creating hemostasis. The femoral artery is usually palpable at the level of the inguinal ligament. Despite this, the ability to control bleeding by application of direct pressure by either the injured combatant or by others including fellow soldiers or medic aides will usually not suffice especially if rapid manual transport must take place. Controlling hemorrhage by application of direct manual pressure may be particularly challenging in cases where there is no large tissue defect allowing for packing and more pressure in closer proximity to the injured vessels. In fact, currently the only way to address this is by exploring the wound site, locating the artery and clamping it with hemostats. For deeper vascular injuries to the pelvis and abdomen, exploration is not an option until the time of surgery.

U.S. Pat. No. 3,933,150 to Kaplan et al. teaches an apparatus for the treatment of shock. The apparatus includes a single piece of double-walled material that can receive pressurized gas. Inflation of the device causes pressure to be exerted on an individual wearing the apparatus, thereby decreasing the volume of pooled venous blood and stabilizing the individual during transport. However, the pressure is exerted is globally or circumferentially and is not specifically directed onto the bleeding site, and thus does little for bleeding from locations that are difficult to access.

U.S. Pat. No. 7,329,792 to Buckman et al., discloses an apparatus for promoting hemostasis, especially of skin-penetrating wounds of the periphery. The device includes fluid impermeable barriers surrounded by exterior dams to be held in place over a wound by applied force. However, such devices are not suited to promote hemostasis in regions that are difficult and thus where it is difficult to exert pressure.

SUMMARY

In accordance with one exemplary aspect, a portable compact hemorrhage occlusion device includes a strap, a base operably connected to the strap, a pressure plate removably attached to the base, and a strap carriage that is linearly translatable relative to the base. A screw assembly is rotatably attached to the base and the screw assembly moves the strap carriage away from the base when the screw assembly is operated in one direction and towards the base when the screw assembly is operated in an opposite direction.

In accordance with another exemplary aspect, an anti-hemorrhage system includes an adjustable strap, a first base operably connected to the adjustable strap, and a first strap carriage that is linearly translatable relative to the first base. A first screw assembly is rotatably attached to the base, the screw assembly moving the strap carriage away from the base when the screw assembly is operated in one direction and towards the base when the screw assembly is operated in an opposite direction. Individual pressure plates in a plurality of pressure plates are each capable of being removably attached to the base.

In accordance with another exemplary aspect a method of applying a portable compact hemorrhage occlusion device includes providing a portable compact hemorrhage occlusion device having a strap, a base, a strap carriage, a screw assembly, and a plurality of removable pressure plates. A pressure plate is selected from the plurality of pressure plates based on a location where pressure is needed. The pressure plate is attached to the base. The strap is wrapped around part of a body. The strap is attached to the strap carriage.

In further accordance with any one or more of the foregoing aspects, a portable compact hemorrhage occlusion device may further include any one or more of the following preferred forms.

In some preferred forms, the portable compact hemorrhage occlusion device includes an anti-rotation bar.

In other preferred forms, the anti-rotation bar prevents relative rotational movement between the strap carriage and the base.

In yet other preferred forms, the pressure plate includes two opposing rails.

In yet other preferred forms, the base includes a flexible arm that selectively secures the pressure plate to the base.

In yet other preferred forms, the two opposing rails each include a wall and an overhang ledge, the base being captured between the walls of the opposing rails and between the overhang ledge and the pressure plate when the pressure plate is attached to the base.

In yet other preferred forms, a screw lock secures the screw assembly in a deployed position.

In yet other preferred forms, the screw lock is a set screw.

In yet other preferred forms, the strap carriage further comprises at least one strap securing opening.

In yet other preferred forms, the strap carriage includes two strap securing openings.

In yet other preferred forms, at least one of the strap securing openings is a slot.

In yet other preferred forms, the strap comprises two bands, one band being located in each strap securing opening.

In yet other preferred forms, the portable compact hemorrhage occlusion device includes a strap lock.

In yet other preferred forms, the strap lock is a set screw.

In yet other preferred forms, the screw assembly includes a handle disposed at one end of the screw assembly.

In yet other preferred forms, the screw assembly includes a first screw and a second screw that is nested within the first screw.

In yet other preferred forms, the first screw has a larger diameter than the second screw.

In yet other preferred forms, the first screw has a hollow central bore with female threads, the female threads cooperating with male threads on an outer surface of the second screw.

In yet other preferred forms, operating the screw assembly to move the strap carriage away from the base causes the strap to tighten around the object to be occluded.

In yet other preferred forms, the plurality of interchangeable pressure plates includes at least two individual pressure plates having different shapes and/or different sizes.

In yet other preferred forms, a first pressure plate has a square or rectangular shape and a second pressure plate has a triangular shape.

In yet other preferred forms, a first pressure plate is removably attached to the base and a second pressure plate is removably attached to the base.

In yet other preferred forms, a second base operationally connected to the adjustable strap, a second strap carriage is linearly translatable relative to the second base, and a second screw assembly is rotatably attached to the second base.

DETAILED DESCRIPTION

Figure 1:
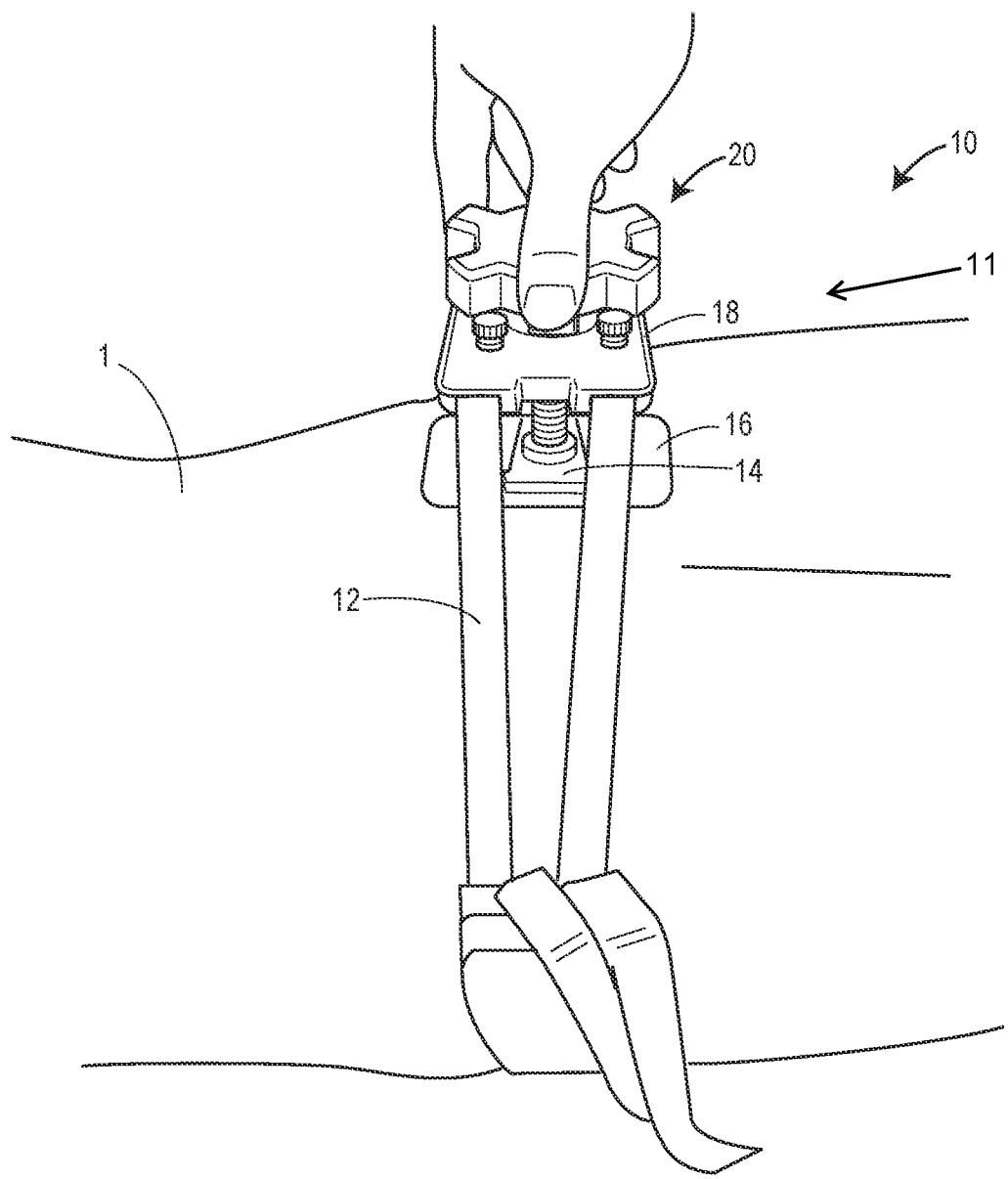
FIG. 1 is a perspective view of a first embodiment of a junctional hemorrhage occlusion device in a deployed position on a patient body.

The disclosed hemorrhage occlusion devices facilitate blood occlusion in patient bodies in emergency situations while enhancing comfort and intuitive use. A screw mechanism in the disclosed hemorrhage occlusion device is selectively lockable, thus allowing for the hemorrhage occlusion device to hold high pressures with very little user effort to ensure that the supply of blood is interrupted to the wound site. Additionally, the disclosed hemorrhage occlusion devices include a removable pressure plate (or plates) that may be selected based on a location and a size of a hemorrhage site.

A strap for the device may comprise a fabric, such as nylon or cotton. Other materials may also be used for the strap. The strap feeds through a pressure assembly which includes a screw assembly, a base, and a strap carriage.

The disclosed hemorrhage occlusion devices provide a portable, small-footprint device that can be used to selectively exert pressure on the body of an injured individual. The device is especially useful in emergency situations, and particularly to apply pressure to areas of the body where it is otherwise difficult to do so. A flexible support portion, such as a belt or strap may be circumferentially attached or secured to an area of the body of an individual in need of applied pressure (e.g. the pelvic area, abdominal area, the chest area, the axillary area, etc.). A pressure assembly is attached to the support portion. The attached pressure assembly is movable or positionable on the support portion i.e. the locations of the pressure assembly on the support portion are not fixed but are mobile, slidable, or otherwise adjustable. For example, the pressure assembly is slidable along a strap to more precisely target pressure to a hemorrhage location. In some embodiments, multiple pressure assemblies may be attached to the support portion to target multiple hemorrhage locations.

After the device is placed on an individual, each pressure assembly can be independently positioned and pressure from each pressure assembly can be independently applied. Upon activation of the pressure assembly, pressure is evenly distributed to the hemorrhage location immediately beneath a pressure plate. Counterexpansion away from the body's surface is prevented or significantly decreased by the nonexpandable nature of the support portion, i.e. the straps retain their dimensions and do not "stretch".

The pressure exerted by the pressure assemblies may be intensified by additional tightening of components (e.g. straps or belts) of the support portion of the device using a tightening means. The benefits of the pressure will vary from application to application. For example, in the case of uncontrolled bleeding from a non-compressible or difficult to compress location, blood vessels in the area are compressed, and bleeding from the compressed vessels is decreased or stopped. In one embodiment, the device is designed to be applied to peripheral areas such as the pelvic region (e.g. inguinal or groin area) to stop bleeding from, for example, femoral and external iliac blood vessels.

Another effect of the screw assemblies is that it also provides support (i.e. stability or rigidity) to the region of the body that it encircles. In fact, the device may be employed chiefly to provide stability and/or pressure, whether or not bleeding is present.

The deployment of the device is rapid and can be carried out by individuals with very little prior training. In fact, a wounded individual in need of such treatment may be able to deploy the device him or herself. The device may thus be used to provide support and/or to stop or lessen bleeding at a trauma site (e.g. on the battlefield, or at the scene of an accident) and during transport to a clinic or hospital where further medical treatment can be provided.

Turning now to the figures, FIG. 1 illustrates one embodiment an anti-hemorrhage system, which includes a junctional hemorrhage control device 10 applied to a patient body 1. The junctional hemorrhage control device 10 includes a strap 12, which in the illustrated embodiment comprises two generally parallel straps, and a pressure assembly 11 removably attached to the strap 12. The pressure assembly 11 comprises a base 14 operably connected to the strap 12, a pressure plate 16 removably attached to the base 14, a strap carriage 18 linearly translatable relative to the base 14 and a screw assembly 20 is rotatably attached to the base 14. The screw assembly 20 moves the strap carriage 18 away from the base 14 when the screw assembly 20 is operated in one direction and towards the base 14 when the screw assembly 20 is operated in an opposite direction.

Figure 2:
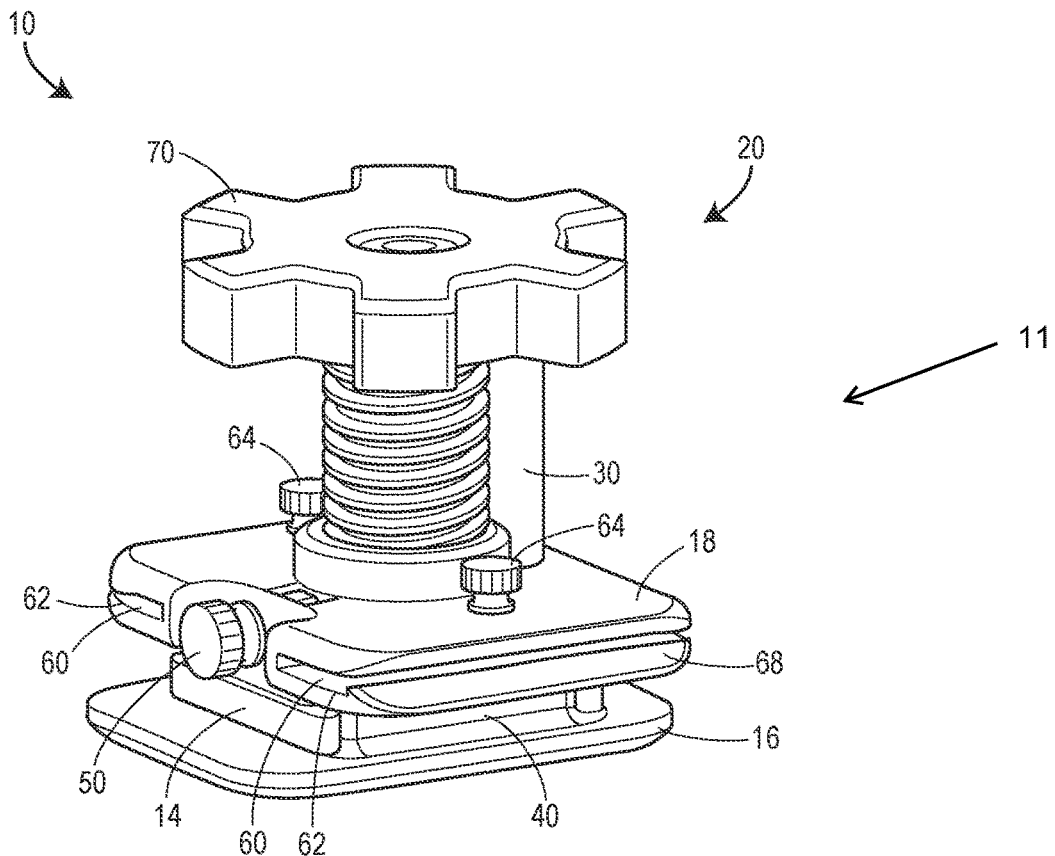
FIG. 2 is a side perspective view of a pressure assembly of the junctional hemorrhage occlusion device of FIG. 1, with the pressure assembly in a retracted position.
Figure 3:
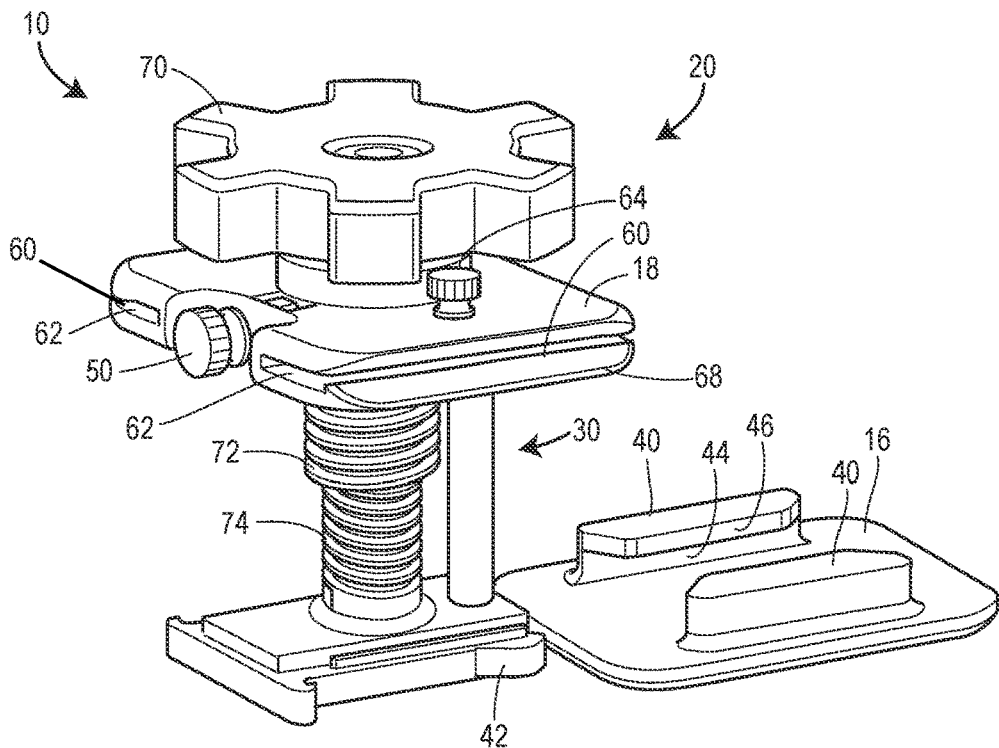
FIG. 3 is a side perspective view of the pressure assembly of FIG. 2, with the pressure assembly in an extended position and a removable pressure plate being separated from the pressure assembly.
Figure 4:
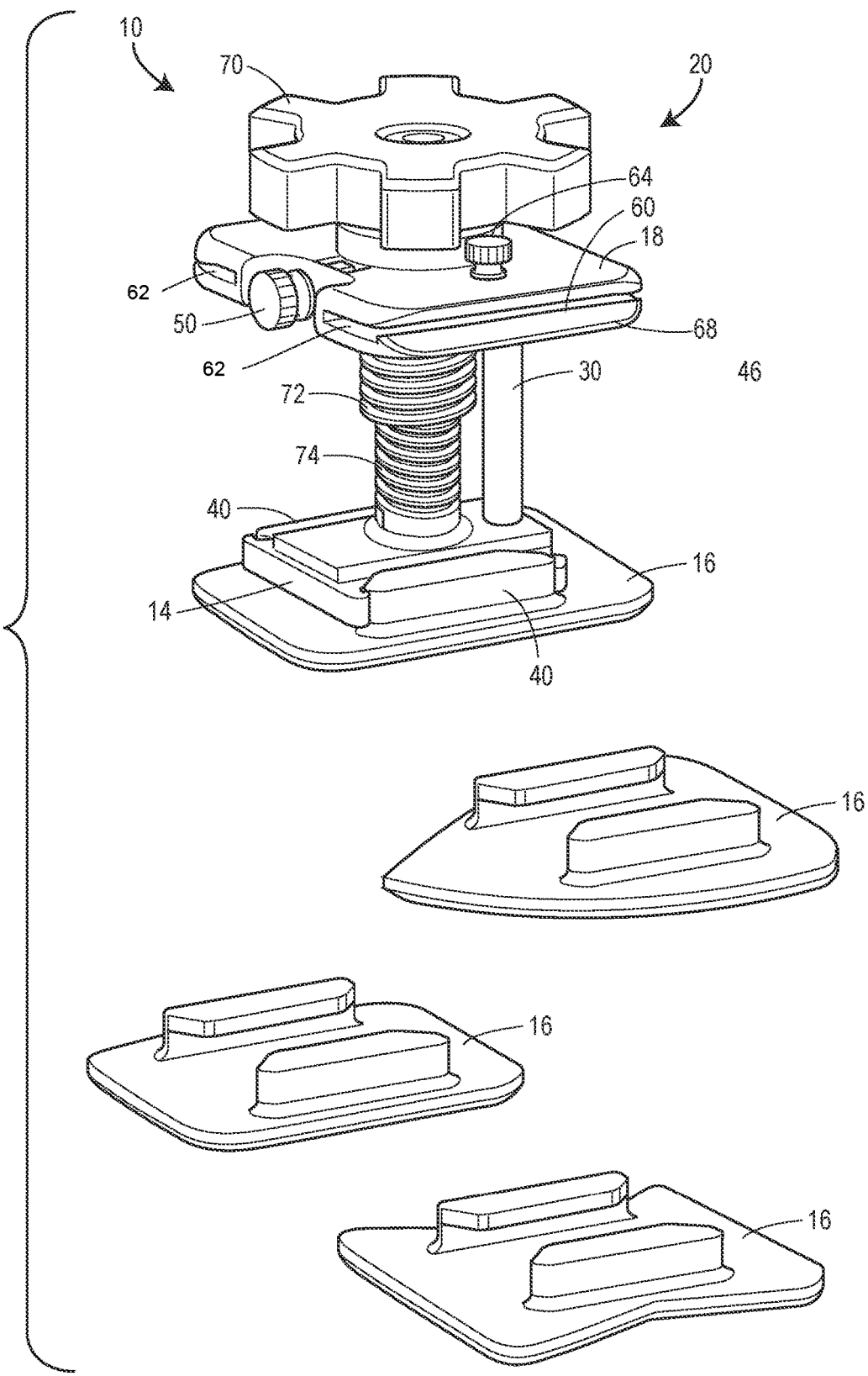
FIG. 4 is a side perspective view of the pressure assembly of FIG. 2, with a plurality of removable pressure plates.

Turning now to FIGS. 2-4, the junctional hemorrhage control device 10 includes an anti-rotation bar 30. The anti-rotation bar 30 prevents or minimizes rotation of the strap carriage 18 when the screw assembly 20 is rotated. The anti-rotation bar 30 also prevents or minimizes relative rotational movement between the strap carriage 18 and the base 14.

The pressure plate 16 is removably attached to the base 14 so that pressure plates 16 having different shapes (FIG. 4) may be removed and replaced based on a needed fit or area to cover a hemorrhage location. The pressure plate 16 may include a connecting structure, such as two opposing rails 40 that guide the pressure plate 16 into position when installing the pressure plate 16 on the base 14. The base 14 includes a flexible arm 42 that selectively secures the pressure plate 16 to the base 14.

The two opposing rails 40 each include a wall 44 and an overhang ledge 46, the base 14 being captured between the walls 44 of the opposing rails 40 and between the overhang ledge 46 and the pressure plate 16 when the pressure plate 16 is attached to the base 14.

A screw lock 50 secures the screw assembly 20 in a deployed position (FIGS. 3 and 4), where the strap carriage 18 is spaced apart from the base 14. In the deployed position, and when secured to the patient body 1, the pressure plate 16 applies pressure towards the patient body 1, over the hemorrhage location, to occlude or reduce blood flow proximate the hemorrhage location. In the illustrated embodiment, the screw lock 50 is a set screw. A user may engage the screw lock 50 when the screw assembly 20 is in the deployed position to prevent the screw assembly 20 from reversing due to the tension on the strap 12 and/or from reversing when unintentional force (such as a bump) is applied to a handle 70. The screw lock 50 also prevents screw assembly 20 reversal from other unintentional outside forces, such as vibration. In some embodiments, the screw lock 50 increases the frictional force against a screw to prevent unintentional screw assembly 20 reversal. By preventing unintentional screw assembly 20 reversal, the screw lock 50 also prevents unintentional translation of the strap carriage 18 relative to the base 14.

The strap carriage comprises at least one strap securing opening 60. In the illustrated embodiment, the strap carriage comprises two strap securing openings 60, one for each strap 12 (FIG. 1). The strap securing openings 60 comprise slots 62 that are sized and shaped to receive at least a portion of the strap 12. More specifically, in the illustrated embodiment, each strap 12 is located in its own slot 62. A pair of lateral platforms 68 may be located proximate the slots 62. The lateral platforms extend outward, away from the strap carriage 18. In some embodiments, the lateral platforms 68 may be angled slightly upward or downward. The lateral platforms 68 provide guiding surfaces for the strap 12 when the strap 12 is inserted into the slots 62.

A strap lock 64 may be located near each slot 62. The strap lock 64 may be engaged to prevent relative movement between the strap carriage 18 and the strap 12 when the pressure assembly 11 is properly positioned along a length of the strap 12. In the illustrated embodiment, the strap lock 64 is a set screw.

The screw assembly 20 includes the handle 70 disposed at one end of the screw assembly 20. The screw assembly 20 includes a first screw 72 and a second screw 74 that is nested within the first screw 72. The first screw 72 has a larger diameter than the second screw 74. The first screw 72 may have a hollow central bore with female threads, the female threads cooperating with male threads on an outer surface of the second screw 74. In other embodiments, the male and female threads may be reversed.

Operating the screw assembly 20 (i.e., turning the handle 70 in a first direction) moves the strap carriage 18 away from the base 14 and causes the strap 12 to tighten and thus pressure to be applied by the pressure plate 16 in a downward direction (i.e., towards the patient body 1) in the figures. Of course, if the junctional hemorrhage control device 10 were located beneath a patient body 1, the pressure would be directed in an upward direction, but still towards the patent body 1.

As illustrated in FIG. 4, a plurality of interchangeable pressure plates 16 may include at least two individual pressure plates 16 having different shapes and/or different sizes. For example, a first pressure plate 16 may have a square or rectangular shape and a second pressure plate 16 may have a triangular shape. Other regular or irregular shapes may also be included in the plurality of interchangeable pressure plates 16 to give an operator a variety of sizes and shapes to choose from to best suit the hemorrhage size and location. Any one of the pressure plates 16 may be removably attached, and thus interchanged with, the base 14.

Figure 5:
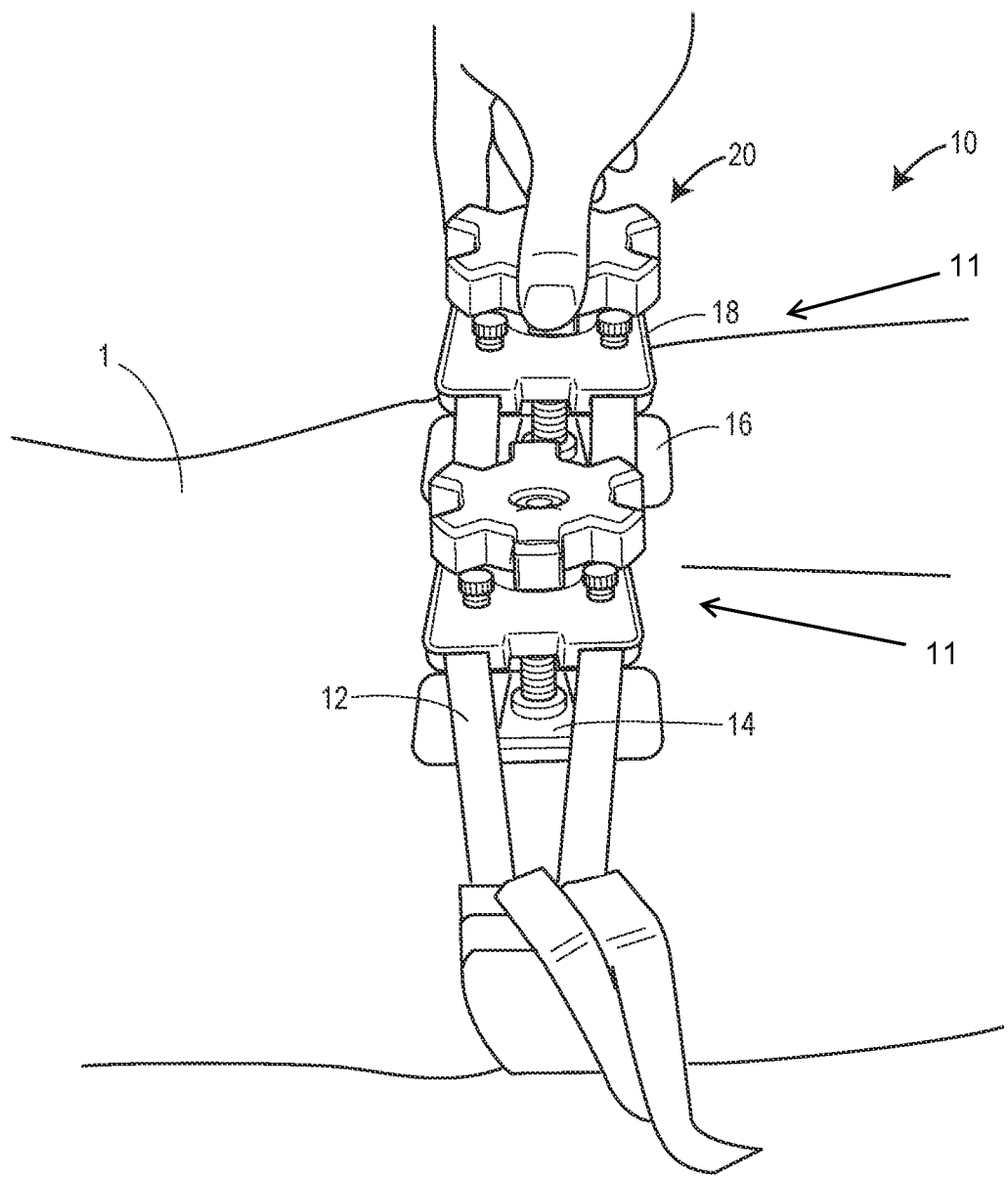
FIG. 5 is a perspective view of a second embodiment of a junctional hemorrhage occlusion device having two pressure assemblies in a deployed position on a patient body.

In yet other embodiments, for example as illustrated in FIG. 5, a second pressure assembly 11 having a second base 14 may operationally be connected to the strap 12 to target a second hemorrhage location. For example, a first pressure assembly 11 may be positioned over the abdomen to occlude a first hemorrhage site and a second pressure assembly 11 may be positioned in the groin area to occlude a second hemorrhage site. The second pressure assembly 11 may have a second strap carriage 18 that is linearly translatable relative to the second base 14, and a second screw assembly 20 that is rotatably attached to the second base 14. The second pressure assembly 11 may have the same elements as the pressure assembly 11 described in FIGS. 1-4.

The junctional hemorrhage control devices 10 described above are particularly useful for occluding hemorrhages in body locations where conventional tourniquets are difficult to apply, for example, in the groin, abdomen, pelvis, and axilla. To occlude a hemorrhage location, the junctional hemorrhage control devices 10 described above are provided and attached to the patient body by wrapping the strap 12 around a portion of the patient body. The pressure assembly 11 is attached to the strap 12 by connecting the strap to the strap carriage 18. A pressure plate 16 is selected from the plurality of pressure plates 16 based on a location where pressure is needed. The pressure plate 16 is attached to the base 14. The screw assembly 20 is then operated to apply pressure to the patient body through the pressure plate 16.

In some embodiments, the screw assembly 20 is sized to provide approximately 1.75-3.5 inches of travel for the strap carriage 18, which is enough vertical travel to ensure that occlusion pressure is reached under all conditions.

If increased torque is required, a larger handle may be used to provide more leverage. In addition to the screw lock, in another embodiment, the disclosed compact hemorrhage control devices advantageously maintain tightening force on the strap so that a user doesn't need to constantly apply the torque to hold the pressure. More specifically, the screw assembly 20, in some embodiments, may include a locking feature, such as a ratchet, which prevents the screw assembly from turning in a loosening direction unless the lock is released. This also allows fine-tuning of the occlusion pressure through tightening at any incremental turning of the screw.

In other embodiments, a writing surface may be provided for recording a time that the hemorrhage control device is applied, which can be important information for a doctor or other medical person to know when evaluating treatment options.

The disclosed junctional hemorrhage control devices advantageously form a hemorrhage control system having a number of interchangeable plates (sizes and shapes) depending on the location of the hemorrhage. For example, smaller square/rectangular plates may be useful for hemorrhage locations in the groin or axilla, while larger triangular or square plates may be useful for the pelvis or abdomen.

The disclosed junctional hemorrhage control devices advantageously may employ more than one base and plate at a time. For example, the disclosed junctional hemorrhage control devices may be configured to occlude a hemorrhage from a single penetrating injury to the groin or axilla and/or be configured to include plates to occlude hemorrhage from bilateral inguinal wounds plus a pelvic would (using two square plates for the inguinal founds and a large triangular plat for the pelvis).

The disclosed junctional hemorrhage control devices are easy to use, generate great mechanical advantage in tightening, and utilize wide bands or straps for less pain and more effective occluding pressures during application. The disclosed hemorrhage control devices are also easily deployable and operable with one hand while operating solely on mechanical power generated by the user, so that a source of electrical power is not needed. Furthermore, due to the compact nature the disclosed hemorrhage control devices are easily portable and generally light weight so that they may be deployed almost anywhere. The removable pressure plates facilitate optimizing the pressure location, which results occlusion pressure being applied more quickly, thereby minimizing blood loss.

While the present invention has been described with respect to a particular embodiment of the present invention, this is by way of illustration for purposes of disclosure rather than to confine the invention to any specific arrangement as there are various alterations, changes, deviations, eliminations, substitutions, omissions and departures which may be made in the particular embodiment shown and described without departing from the scope of the claims.

What is claimed is:

1. A portable compact hemorrhage occlusion device comprising:
    a strap;
    a base operably connected to the strap;
    a pressure plate attached to the base;
    a strap carriage that is linearly translatable relative to the base; a screw assembly that is rotatably attached to the base; and
    an anti-rotation bar,
    wherein the screw assembly moves the strap carriage away from the base when the screw assembly is operated in one direction and towards the base when the screw assembly is operated in an opposite direction, and
    wherein the anti-rotation bar prevents relative rotational movement between the strap carriage and the base.

2. The portable compact hemorrhage occlusion device of claim 1, wherein the pressure plate is removable and includes two opposing rails.

3. The portable compact hemorrhage occlusion device of claim 2, wherein the two opposing rails each include a wall and an overhang ledge, the base being captured between the walls of the opposing rails and between the overhang ledges and the pressure plate when the pressure plate is attached to the base.

4. The portable compact hemorrhage occlusion device of claim 1, further comprising a screw lock that secures the screw assembly in a deployed position.

5. The portable compact hemorrhage occlusion device of claim 4, wherein the screw lock is a set screw.

6. The portable compact hemorrhage occlusion device of claim 1, wherein the strap carriage further comprises at least one strap securing opening.

7. The portable compact hemorrhage occlusion device of claim 6, wherein the at least one strap securing opening is a slot.

8. The portable compact hemorrhage occlusion device of claim 6, further comprising a strap lock.

9. The portable compact hemorrhage occlusion device of claim 8, wherein the strap lock is a set screw.

10. The portable compact hemorrhage occlusion device of claim 1, wherein the screw assembly includes a first screw and a second screw that is nested within the first screw.

11. The portable compact hemorrhage occlusion device of claim 10, wherein the first screw has a larger diameter than the second screw.

12. The portable compact hemorrhage occlusion device of claim 10, wherein the first screw has a hollow central bore with female threads, the female threads cooperating with male threads on an outer surface of the second screw.

13. A portable compact hemorrhage occlusion device, comprising:
    a strap;
    a base operably connected to the strap;
    a pressure plate attached to the base;
    a strap carriage that is linearly translatable relative to the base; and
    a screw assembly that is rotatably attached to the base,
    wherein the screw assembly moves the strap carriage away from the base when the screw assembly is operated in one direction and towards the base when the screw assembly is operated in an opposite direction, and
    wherein the base includes a flexible arm that selectively secures the pressure plate to the base.

14. A method of applying a portable compact hemorrhage occlusion device, the method comprising:
    providing a portable compact hemorrhage occlusion device including a strap, a base, a strap carriage, a screw assembly, and a pressure plate removably attached to the base;
    wrapping the strap around part of a body;
    sliding the strap into the strap carriage; and
    fixing the strap in position relative to the strap carriage,
    wherein the base includes a flexible arm that selectively secures the pressure plate to the base.

15. The method of claim 14, further comprising selecting the pressure plate from a plurality of pressure plates, based on a limb location where pressure is needed and removably attaching the pressure plate to the base.

16. An anti-hemorrhage system comprising:
an adjustable strap;
a first base operationally connected to the adjustable strap;
a first strap carriage that is linearly translatable relative to the first base, the first strap carriage comprising a first strap securing opening;
a first screw assembly that is rotatably attached to the first base; and
a pressure plate being capable of being removably attached to the first base,
wherein the first screw assembly moves the first strap carriage away from the first base when the first screw assembly is operated in one direction and towards the first base when the first screw assembly is operated in an opposite direction, and
wherein the first base includes a flexible arm that selectively secures the pressure plate to the first base.

17. The anti-hemorrhage system of claim 16, further comprising a plurality of removable pressure plates, wherein a first pressure plate in the plurality of removable pressure plates has a square or rectangular shape and a second pressure plate in the plurality of removable pressure plates has a triangular shape.

18. The anti-hemorrhage system of claim 16, further comprising
a second base operationally connected to the adjustable strap;
a second strap carriage that is linearly translatable relative to the second base; and
a second screw assembly that is rotatably attached to the second base.

* * * * *